United States Patent [19]

Young

[11] 3,968,010
[45] July 6, 1976

[54] MICROBIOLOGICAL CULTURING METHOD AND MEANS

[75] Inventor: Frank Edward Young, Pittsford, N.Y.

[73] Assignee: Miles Laboratories, Inc., Elkhart, Ind.

[22] Filed: Dec. 8, 1975

[21] Appl. No.: 638,652

[52] U.S. Cl. .......................... 195/103.5 R; 195/127; 195/100; 195/102
[51] Int. Cl.² .......................................... C12K 1/06
[58] Field of Search............. 195/103.5 R, 100, 102, 195/127

[56] References Cited
UNITED STATES PATENTS

| | | | |
|---|---|---|---|
| 3,107,204 | 10/1963 | Brown et al. | 195/103.5 R |
| 3,876,503 | 4/1975 | Mennen | 195/103.5 R |

*Primary Examiner*—Alvin E. Tanenholtz
*Attorney, Agent, or Firm*—Andrew L. Klawitter

[57] ABSTRACT

An improved method and means for culturing an osmotically fragile microorganism in contact with a rehydrated nutrient-incorporated web matrix, which comprises rehydrating said matrix with an aqueous liquid containing a water soluble polyhydric alcohol prior to or simultaneous with the inoculation of the matrix. The polyhydric alcohol is preferably of the general formula $$HOCH_2 - (CHOH)_n - CH_2OH$$

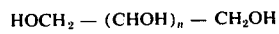

Wherein $n = 0$–4, which includes such substances as ethylene glycol and glycerol. Rehydration of the nutrient-incorporated web matrix with an aqueous liquid containing a polyhydric alcohol greatly enhances the reproducibility of the culturing method, the polyhydric alcohol serving primarily as a protective agent against fatal osmotic shock to the microorganism.

22 Claims, 3 Drawing Figures

MICROBIOLOGICAL CULTURING METHOD AND MEANS

BACKGROUND OF THE INVENTION

1. Field of the Invention

This invention relates to methods and means for culturing or detecting microorganisms in contact with a nutrient-incorporated web matrix.

In the diagnosis of microbial derived diseased conditions in man and animals, it is often highly useful to determine the particular causative microorganisms. This is particularly true in the diagnosis of the venereal disease gonorrhea which is the direct result of infection with the microorganism *Neisseria gonorrhoeae*. Many methods have evolved from the search for specific microbial identification tests, including the use of colorimetric indicators and immunochemical indicators. Nonetheless, the conventional diagnosis of certain microbial derived diseases remains based on microbiological culture techniques.

2. Description of the Prior Art

Conventional microbiological techniques used in diagnosis of microbial derived diseases involve an in vitro culturing of a test sample obtained from the subject under diagnosis. The culturing media used may be either capable of supporting the growth of a broad spectrum of microorganisms or selective to a small number of microorganisms or even a single strain of microorganism. Generally the object of using an all-purpose medium is to isolate pure colonies from the sample and thereafter to analyze them either chemically or biologically in order to identify pathological microorganisms in the sample. When a selective media is used, one knows if a certain group or variety of microorganisms is present or absent in the sample based on a growth or no-growth observation. It is therefore critical to such microbiological techniques to have available appropriate culturing techniques for those microorganisms of pathological significance.

The contemporary clinical laboratory is in great need of more rapid and convenient culturing methods and means. At the present time, clinical microbiological techniques are based almost exclusively on the use of poured agar plates. It is well known that such agar plates have a very short shelf life and are extremely cumbersome to use. Some synthetic gels have been developed as proposed substitutes for the agar base in the poured plates but they have not been proven to be any more stable or easy to use. Just recently, culturing devices comprising a nutrient-incorporated web matrix or absorbent pad have been developed which have proven to be useful substitutes for the disadvantageous agar plates. Such devices provide a substantially dry web matrix incorporated with microbiological nutrients which can be stored for many months and then rehydrated for use in the culturing of microorganisms. Such a device is described in U.S. Pat. No. 3,881,993 assigned to the assignee hereof.

These devices have been found to be adaptable for the cultivation of a wide variety of microorganisms, including fairly fastidious microorganisms, i.e., those requiring very carefully controlled nutrient media and/or atmospheres. For instance, a highly useful culturing means has been designed based on the use of a nutrient-incorporated web matrix for the growth and detection of the delicate microorganism *Neisseria gonorrhoeae* as disclosed in U.S. Pat. No. 3,888,741, also assigned to the assignee hereof.

The matrix culturing devices of the prior art have not been entirely satisfactory, however, for use in the culturing of osmotically sensitive microorganisms. In the web matrix type devices, the growing microorganisms are more or less surrounded by a liquid environment and may be found dispersed throughout the interior portion of the web matrix, in contrast to conventional agar plates where the growing microorganisms are supported on the gel surface. Because of this critical distinction, it has been found that in order to prepare a useful web matrix type culturing device to correspond to a particular conventional agar plate, it is oftentimes not merely a simple matter of incorporating the nutrient ingredients from the agar medium formulation into a web matrix structure. One instance where this has been found to be the case is in the culturing of osmotically fragile microorganisms, particularly *N. gonorrhoeae*.

SUMMARY OF THE INVENTION

It has now been found that osmotically fragile microorganisms can be advantageously cultured using nutrient-impregnated web matrix or absorbant pad type devices by including a water soluble polyhydric alcohol in the liquid used to rehydrate the substantially dry water-absorbent web matrix. Rehydration of the dry web matrix at the time of use is accomplished either prior to or simultaneous with the inoculation of the web matrix with either the microorganism to be cultured or a test specimen suspected of containing a particular type or variety of microorganism to be detected. In this way, the microorganism, upon contact with the web matrix, is already or is assured of being dispersed into an aqueous environment containing the protective polyhydric alcohol.

Based on the information presently at hand, it is theorized that the polyhydric alcohol serves in a protective capacity due to its ability to equalize the osmotic pressure exerted on the microorganism by the aqueous environment. In addition, the polyhydric alcohols which have the features of a humectant have been found to be particularly useful, as they appear to further stabilize and retain moisture in the rehydrated web matrix. An additional advantage of using a rehydration fluid containing a polyhydric alcohol, particularly glycerol, is that removal of colonies from the matrix after incubation is more easily and reproducibly accomplished than when a polyhydric alcohol is not included in the rehydration fluid. Ready removal of developed colonies is particularly valuable where further cultivation or analysis is desirable, such as where antimicrobial susceptibility tests or confirmatory identification tests are indicated.

The present invention also provides culturing means comprising (1) a substantially dry, water-absorbent web matrix incorporated with microbiological nutrient material sufficient to support growth of the desired variety or varieties of microorganisms and (2) a volume of an aqueous liquid containing a water soluble polyhydric alcohol to serve as the rehydration fluid. The web matrix may be associated with holding and/or enclosing means to form integral culture devices useful for the cultivation of various types of microorganisms under various atmospheres. Such culturing devices and the inventive rehydration liquid may also be combined with various indicator devices to provide test kits useful for the presumptive identification of a particular type or variety of microorganism.

DESCRIPTION OF THE PREFERRED EMBODIMENTS

Figure 1:
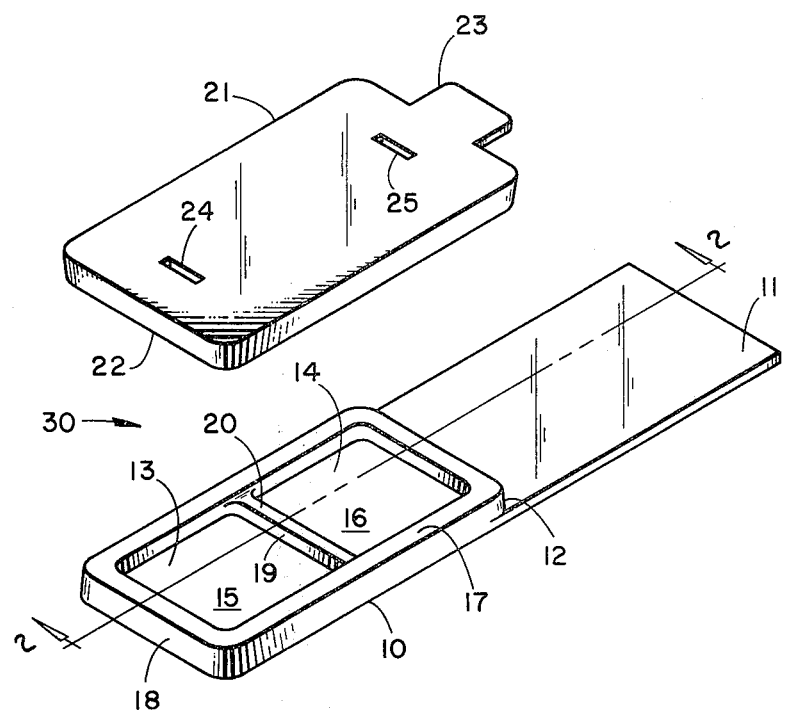
FIG. 1 is an exploded perspective view of a preferred form of a culture device constructed in accordance with the present invention.

The preferred polyhydric alcohols include the glycols, in particular those which have a skeleton of between 2 and 6 carbon atoms, and the compounds of the general formula

$$HOCH_2-(CHOH)_n-CH_2OH.$$

Useful glycols which have a skeleton of between 2 and 6 carbon atoms include ethylene glycol (which is particularly preferred), propylene glycol, trimethylene glycol, α-butylene glycol, β-butylene glycol, 1,3-butanediol, tetramethylene glycol, isobutylene glycol, 1,5-pentanediol, 3-methyl-1,3-butanediol, pinacol, and 2-methyl-2,4-pentanediol. Useful compounds having the above-mentioned general formula include glycerol ($n=1$) (which is particularly preferred), erythritol ($n=2$), adonitol and arabitol ($n=3$), sorbitol and mannitol ($n=4$), and perseitol ($n=5$). Also, it should be noticed that ethylene glycol may be considered to be of the general formula mentioned above where $n=0$. The preferred polyhydric alcohols are those of the above-mentioned general formula wherein $n=0-4$. The polyhydric alcohol is water soluble and non-bacteriocidal, and preferably in its pure state is a slightly to moderately viscous liquid. Those polyhydric alcohols which are humectants, such as ethylene glycol and glycerol, have the additional advantageous feature of stabilizing and retaining moisture in the rehydrated nutrient-incorporated web matrix.

The polyhydric alcohol may be contained in an aqueous liquid which is used to rehydrate the web matrix prior to or simultaneously with inoculation of the web matrix with the microorganism or test specimen, or it may be contained in an aqueous liquid which itself serves as the inoculation medium by also including the microorganism or test specimen. In the first situation, inoculation is accomplished by contact of the matrix with an inoculum such as an isolated microorganism or colony thereof, a broth or aqueous suspension of microorganism, a liquid test specimen such as urine or serum, a swab or loop needle specimen, and so forth. In the second situation, the inoculum, as described above, is added to the rehydration liquid, thus resulting in simultaneous rehydration and inoculation of the web matrix upon contact therewith.

The concentration of the polyhydric alcohol in the rehydration liquid may vary widely depending upon the particular polyhydric alcohol chosen and the particular microorganism or variety of microorganisms to be cultured or detected. Generally, however, the polyhydric alcohol is preferably present in the rehydration liquid in an amount sufficient to produce a concentration of between about 1 and about 6, and preferably about 5, percent by weight to volume in the rehydrated and inoculated web matrix. Therefore, where the inoculum is in a form other than a liquid, and thus where dilution of the rehydration fluid in the rehydrated web matrix is not a factor, the rehydration liquid itself preferably contains between about 1 and about 6 percent by weight to volume of the polyhydric alcohol.

Microbiological nutrient material which is incorporated with the web matrix, such as by impregnation therein or adsorption therewith, includes the conventional substances which actively participate in supporting the viability and growth of a desired microorganism. Materials which inhibit or retard growth of undesirable microorganisms may also be included in the web matrix. As a result, the nutrient-impregnated web matrix may comprise an all-purpose general medium capable of supporting a wide spectrum of microorganisms or may comprise a selective medium such as where the culturing method and means are used in detection of a particular type or variety of microorganism. An example of a selective medium is that generally known as Thayer-Martin media which is selective for *N. gonorrhoeae*.

The culturing means of the present invention, in combination with an indicator pad incorporated with an indicator reactable with a group or variety of microorganisms, provides a convenient test means for presumptively identifying microorganisms in a sample. The indicator may react with the microorganism or with a metabolic product or other substance released by the microorganism. Tetrazolium salts and pH sensitive reagents are examples of indicators useful for this purpose. It is known that *N. gonorrhoeae* microorganisms contain an extra-cellular oxidase enzyme specifically reactable with certain indicators conventionally known as cytochrome oxidase indicators. Hence, such indicators are useful in the present invention when *N. gonorrhoeae* organisms are the subject of the test. Exemplary of these indicators are p-amino dimethylaniline, dimethyl phenylenediamine, N,N,N',N'-tetramethyl-p-phenylenediamine dihydrochloride, dimethyl-p-phenylenediamine oxalate, and a mixture of dimethyl phenylenediamine and alpha-naphthol.

Figure 2:
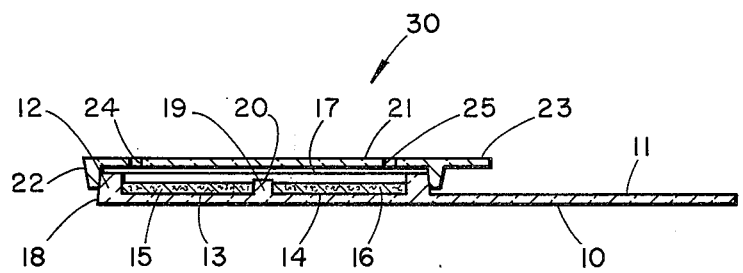
FIG. 2 is a longitudinal cross-sectional view of the culture device depicted in FIG. 1 in its unexploded state, such view being taken along line 2—2 of FIG. 1.

Reference is made at this point to the drawing in order to illustrate one form of culture device 30 useful in the practice of the present invention. FIGS. 1 and 2 show a culture device comprising a rectangular base or receptacle member 10 and a cooperable rectangular cover member 21. Base member 10 has an elongated rectangular plate-like bottom wall 11 having formed on one end portion thereof an upstanding annular rectangular wall 12. The wall 12 has a planar upper surface generally parallel with the bottom wall 11 and has an outer surface 18 which tapers inwardly from bottom to top as shown in the drawing. Base member 11 is also formed with an upstanding transverse wall 19 having an upper surface 20 spaced below the plane of upper surface 17 and generally parallel therewith. Walls 12 and 19 define spaced rectangular wells 13 and 14. Nutrient-incorporated web matrices or pads 15 and 16 are disposed in wells 13 and 14, respectively.

Figure 3:
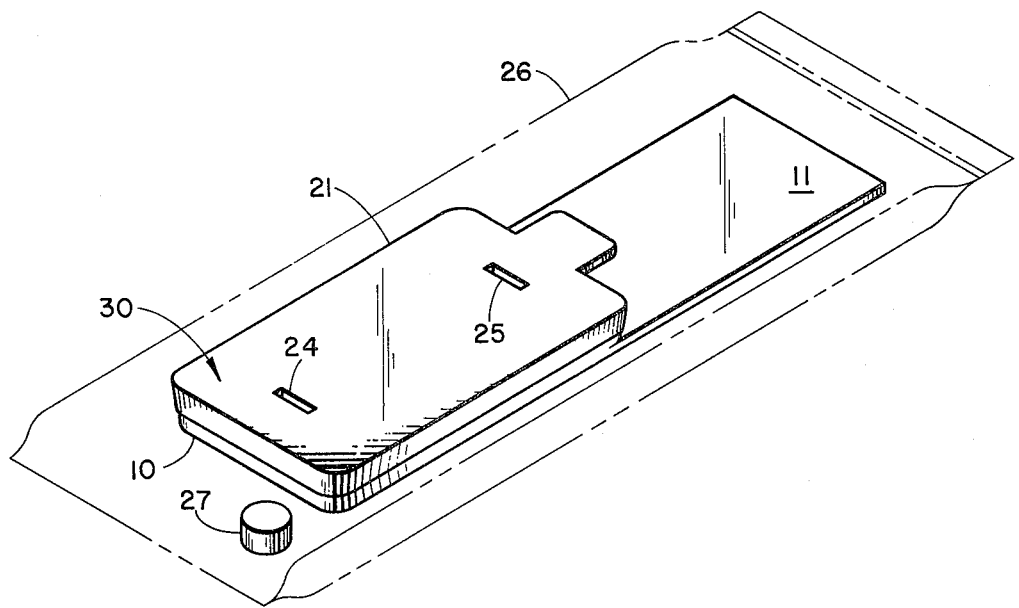
FIG. 3 is a perspective view of a preferred form of an assemblage constructed in accordance with the present invention and including the culture device depicted in FIG. 1, a gas generating tablet, and enclosure means, the latter being shown in phantom.

A cover member 21 has a rectangular annular depending flexible lip portion 22 which is telescopically frictionally engageable with the upper portion of the outer surface 18 of wall 12. Vent slots 24 and 25 are provided in cover member 21 generally adjacent opposite ends thereof to permit the flow of circumambient atmospheric gas into and out of the chamber formed when cover member 21 is positioned on the base member 10 as shown in FIGS. 2 and 3. Cover member 21 is also provided with finger tab 23 to facilitate disengagement of cover member 21 from the base member 10.

Base member 10 and cover 21 may be made out of any suitable material, organoplastics being preferred. For example, base member 10 may be made from a relatively rigid organoplastic such as polystyrene, and cover 21 may be made of a relatively more flexible organoplastic such as polyethylene. It will be observed that when the cover 21 is in place on base member 10 as shown in FIG. 3, said cover and base member cooperate to provide a vented chamber containing nutrient-incorporated pads 15 and 16.

One method of use wherein a test specimen is cultured under a gas enriched atmosphere will now be described. Cover member 21 and base member 10 are disengaged, and a rehydrating volume of an aqueous liquid containing a polyhydric alcohol such as glycerol is added dropwise to pads 15 and 16, respectively. Each of pads 15 and 16 is then inoculated with a swab specimen by a forceful rolling movement of the swab across the surfaces of pads 15 and 16. Cover member 21 is engaged with base member 10 as shown in FIG. 3, and the assembled device 30 is inserted into a sealable envelope such as the envelope 26 shown in FIG. 3, which envelope may take the form of an aluminum foil pouch. A gas generating tablet 27, such as a carbon dioxide generating tablet comprising sodium bicarbonate and citric acid, is also placed in the envelope 26, which envelope is then sealed and placed in an incubator. After a predetermined incubation period, the culture device 30 is removed from the pouch and cover member 21 disengaged therefrom by means of finger tab 23. The surface of nutrient-incorporated pad 15 is then firmly and momentarily contacted with the surface of an indicator pad incorporated with a reagent reactable with the microorganism to be detected to give an observable response. The remaining pad 16 may be used for the purpose of further examination or analysis of the grown culture or may be incubated for an additional period of time by reinserting culture device 30 into pouch 26 and returning the assembled article to the incubator.

The foregoing method can also be practiced by the use of an alternative form of culture device 30 wherein a carbon dioxide generating pad of the type disclosed in U.S. Pat. No. 3,888,741 is substituted for one of the nutrient-incorporated pads 15 or 16. In the latter form of test device the vent slots 24 and 25 are omitted from cover member 21. In use, the nutrient-incorporated pad is inoculated as before and the non-vented cover member placed on the base member 10. The assembled article is then placed under suitable incubation conditions. A culture device of this type is more fully described in U.S. Pat. No. 3,888,741 assigned to the assignee hereof.

The culturing means and method of the present invention is useful in the culturing and/or detection of a wide variety of microorganisms, particularly those which exhibit some degree of osmotic fragility. Exemplary of the latter class of microorganisms are those of the genus *Neisseria*, particularly *N. meningitidis* and *N. gonorrhoeae*. The culture and detection of the osmotically fragile microorganism *N. gonorrhoeae* using nutrient-incorporated web matrix type devices has been particularly improved using the method and means of the present invention.

The present invention will now be illustrated, but is not intended to be limited, by the following Example.

EXAMPLE

A. Preparation of Culture Devices

Culture pads selective for *N. gonorrhoeae* were prepared as follows:

1. A 100 ml aqueous solution, designated as Solution A, was prepared to contain the following ingredients:

| | |
|---|---|
| Proteose Peptone No. 3* | 6.0 gm |
| water soluble starch | 0.2 gm |
| dipotassium phosphate | 0.8 gm |
| monopotassium phosphate | 0.2 gm |
| sodium chloride | 1.0 gm |

*Difco Laboratories, Inc., Detroit, Michigan

The solution was heated to boiling on a hot plate equipped with a magnetic stirrer and was steam sterilized in an autoclave at about 121°C for about 15 minutes. The sterilized solution was allowed to cool to about 45°C, at which time 6 ml of IsoVitaleX enrichment solution was added (IsoVitaleX is available from BBL, Division of Becton, Dickinson and Co., Cockeysville, Md.).

2. A second solution, designated as Solution B, was prepared as follows: To 2 gm of commercial hemoglobin was added 100 ml of cold water. The resulting hemoglobin solution was heated to boiling on a hot plate equipped with a magnetic stirrer and filtered. The filtrate was steam sterilized in an autoclave at about 121°C for about 15 minutes.

3. Solutions A and B were combined and the following antibiotics added in amounts sufficient to attain the indicated concentrations in the resulting solution:

| | |
|---|---|
| Vancomycin (Eli Lilly and Co., Indianapolis, Indiana) | 4 mg/ml |
| Sodium colistimethate (Warner-Lambert Co., Morris Plains, New York) | 40 mg/ml |
| Amphotericin B (Grand Island Biologicals Co., Grand Island, New York) | 5 mg/ml |
| Trimethoprim (Hoffman-LaRoche Inc., Rochester, New York) | 5 mg/ml |

4. A sheet of S and S 470 paper, manufactured by Schleicher and Schuell, Inc., Keene, N.H., was impregnated with the solution resulting from step 3 and was then dried for 2–3 hours in a forced air oven at about 35°C. Rectangular pads 15 and 16 were cut from the dry nutrient-impregnated sheet to fit in wells 13 and 14 of base member 10 of the device 30 shown in FIGS. 1 and 2. One pad was press fitted into each of the wells 13 and 14 for each device 30 prepared. The vented cover 21 was then applied to each base member 10 and the assembled devices were sterilized by gamma irradiation.

B. Effect of 5 Percent Glycerol in the Rehydration Liquid on the Growth on *N. gonorrhoeae*

The performance of the culture pads when rehydrated with an aqueous 5 percent (weight to volume)

glycerol solution in comparison to that of culture pads rehydrated with distilled water was determined using, as inocula, aqueous suspensions of four different varieties of N. gonorrhoeae. One variety was obtained from a clinical specimen and the other three were obtained from the Center for Disease Control, Atlanta, Ga., and were identified by CDC Nos. 115, 116, and 117 respectively.

A test panel was set up for each of the four varieties of microorganisms, each of the test panels comprising two or more test sets. Each test consisted of an equal number of (a) control agar plates containing conventional Thayer-Martin media prepared according to the method described in *Public Health Reports* 82:361(1967), (b) culture pads in devices 30 prepared as in Part A above, rehydrated with distilled water, and (c) culture pads in devices 30 prepared as in Part A above, rehydrated with an aqueous 5 percent (weight to volume) glycerol solution. Each plate and culture pad in each test set was inoculated with a 0.1 ml aqueous broth suspension of the particular variety of N. gonorrhoeae assigned to the test panel to which the plate or culture pad belonged. The amount of N. gonorrhoeae in the suspension varied from one test set to another to enable analysis of the culture pad performance at various levels of inocula. All of the plates and culture pads in the four test panels were incubated overnight under carbon dioxide atmospheres as follows: The plates were placed in a carbon dioxide incubator. Each device 30, with its vented cover 21 in position on its base member 10, was inserted into an aluminum foil pouch 26 along with a carbon dioxide releasing tablet 27. The pouches 26 were than sealed and placed in a conventional incubator.

After the incubation period, a colony count was performed on each plate and the number of colonies counted was recorded. The notation "TNTC" was used to indicate those instances where the number of colonies was too numerous to count. The surface of each of the culture pads was then firmly and momentarily contacted with the surface of a cytochrome oxidase indicator pad prepared according to the method described in U.S. Pat. No. 3,888,761 (Example 4, Part A). The performance of the culture pads was then determined using the following scoring code: Pads which did not produce an observable color response were given a score of "0"; pads which produced between 1 and 5 discrete, purple-colored colony locations were given a score equal to the number of colony locations observable; and pads producing an observable response exceeding 5 discrete colony locations were given a score of between 6 and 20 based on a comparison with an arbitrary response chart consisting of two response blocks. One block represented a large number of discrete, observable colony locations and was assigned a scoring code of "10," and the other block represented a confluent purplish smudge and was assigned a scoring code of "20." Responses in between the response blocks were interpolated for scoring code purposes. The results are given in Table 1 and indicate that the presence of glycerol in the rehydrating fluid greatly enhances the reproducibility of the test results produced with culture pads.

TABLE 1

| Microorganism (N. gonorrhoeae) | Plate Count of Inoculum | Total No. of Test Sets | Visual Results Using Rehydrated Culture Pads | | | |
|---|---|---|---|---|---|---|
| | | | No Glycerol | | 5% Glycerol | |
| | | | No. of Tests | Response | No. of Tests | Response |
| Clinical Isolate | TNTC | 5 | 3 | 20 | 5 | 20 |
| | | | 1 | 10 | | |
| | | | 1 | 5 | | |
| | TNTC | 10 | 5 | 15* | 10 | 15 |
| | | | 1 | 5 | | |
| | | | 1 | 2 | | |
| | | | 1 | 1 | | |
| | 200 | 10 | 8 | 10 | 8 | 15 |
| | | | 1 | 1 | 1 | 5 |
| | | | 1 | 0 | 1 | 1 |
| | 20 | 10 | 1 | 5 | 10 | 5 (av. of ten spots per pad) |
| | | | 4 | 1 | | |
| | | | 5 | 0 | | |
| CDC No. 115 | TNTC | 6 | 1 | 10 | 6 | 15 |
| | | | 3 | 5 | | |
| | | | 2 | 0 | | |
| | 500 | 6 | 1 | 10 | 2 | 15 |
| | | | 3 | 5 | 4 | 10 |
| | | | 1 | 2 | | |
| | | | 1 | 0 | | |
| | 72 | 6 | 1 | 4 | 4 | 10 |
| | | | 2 | 2 | 2 | 4 |
| | | | 3 | 0 | | |
| CDC No. 116 | TNTC | 6 | 4 | 15 | 6 | 20 |
| | | | 1 | 10 | | |
| | | | 1 | 5 | | |
| | 1000 | 6 | 3 | 15** | 5 | 15** |
| | | | 2 | 4 | | |
| | | | 1 | | | |
| | 150 | 6 | 1 | 10 | 5 | 10 |
| | | | 1 | 4 | 1 | 5 |
| | | | 4 | 1 | | |
| CDC No. 117 | 1000 | | 1 | 15 | 6 | 20 |
| | | | 2 | 10 | | |
| | | | 1 | 7 | | |
| | | | 2 | 5 | | |
| | 100 | | 3 | 5 | 1 | 15 |
| | | | 1 | 2 | 3 | 10 |
| | | | 2 | 0 | 1 | 5 |

TABLE 1-continued

| Microorganism (N. gonorrhoeae) | Plate Count of Inoculum | Total No. of Test Sets | Visual Results Using Rehydrated Culture Pads | | | |
|---|---|---|---|---|---|---|
| | | | No Glycerol | | 5% Glycerol | |
| | | | No. of Tests | Response | No. of Tests | Response |
| | | | 1 | | 1 | |

*two pads missing
**one pad missing

C. Effect of Various Levels of Glycerol in the Rehydration Liquid on the Growth of N. gonorrhoeae Two test panels similar to those described in Part B above were run using, respectively, N. gonorrhoeae CDC No. 116 and another variety of N. gonorrhoeae obtained from the Center for Disease Control and designated CDC No. 111. The only significant difference between the two test panels described in this Part C and those described in Part B above was that the inoculum suspension contained 4 percent (weight to volume) glycerol and 3% Trypticase Soy Broth nutrient (available from BBL, Division of Becton, Dickinson and Co., Cockeysville, Md.). In addition, for each test set there were four groups of culture pads rather than two, each of which were rehydrated with a different one of the following liquids: distilled water, an aqueous 5 percent glycerol solution, an aqueous 7.5 percent glycerol solution, and an aqueous 10 percent glycerol solution. After inoculation with the glycerol-containing suspension, the four groups of culture pads contained, due to the dilution factor, the following concentrations of glycerol respectively, 1, 4.75, 6.6, and 8.5 percent. The results are given in Table 2 and indicate that glycerol levels above about 6 percent in the rehydrated-/inoculated pads have a deleterious effect on the growth of N. gonorrhoeae.

What is claimed is:
1. In a method for culturing or detecting an osmotically fragile microorganism which comprises the steps of rehydrating a substantially dry, water-absorbent, nutrient-incorporated matrix by contact with an aqueous liquid, simultaneously or subsequently contacting said matrix with said microorganism or with a test specimen suspected of containing said microorganism, and thereafter incubating said test specimen in contact with the rehydrated matrix, the improvement which comprises including in said rehydrating aqueous liquid a water soluble polyhydric alcohol.

2. A method as claimed in claim 1 wherein said polyhydric alcohol has the general formula $$HOCH_2-(CHOH)_n-CH_2OH$$

wherein $n = 0-4$.

3. A method as claimed in claim 1 wherein said polyhydric alcohol is glycerol.

4. A method as claimed in claim 3 wherein glycerol is present in said aqueous rehydration liquid at a concentration of between about 1 and about 6 percent by weight to volume.

5. A method as claimed in claim 3 wherein glycerol is present in said aqueous rehydration liquid at a concentration of about 5 percent by weight to volume.

6. A method as claimed in claim 1 wherein said polyhydric alcohol is present in said aqueous rehydration liquid at a concentration of between about 1 and about 6 percent by weight to volume.

7. Means for culturing an osmotically fragile microorganism comprising a substantially dry, water-absorbent matrix incorporated with microbiological nutrient material sufficient to support the growth of said microorganism, and an aqueous rehydration liquid therefor containing a water soluble polyhydric alcohol.

8. Culturing means as claimed in claim 7 where said polyhydric alcohol has the general formula $$HOCH_2-(CHOH)_n-CH_2OH$$

wherein $n = 0-4$.

9. Culturing means as claimed in claim 7 wherein said polyhydric alcohol is glycerol.

10. Culturing means as claimed in claim 9 wherein glycerol is present in said aqueous liquid at a concentration of between about 1 and about 6 percent by weight to volume.

11. Culturing means as claimed in claim 9 wherein glycerol is present in said aqueous liquid at a concentration of about 5 percent by weight to volume.

TABLE 2

| Microorganism (N. gonorrhoeae) | Plate Count of Inoculum | Total No. of Test Sets | Visual Results Using Rehydrated Culture Pads Percent Glycerol in Rehydrated/Inoculated Pad | | | | | | | |
|---|---|---|---|---|---|---|---|---|---|---|
| | | | 1% | | 4.75% | | 6.6% | | 8.5% | |
| | | | No. of tests | Response | No. of tests | Response | No. of tests | Response | No. of tests | Response |
| CDC No. 116 | TNTC | 10 | 10 | 20 | 10 | 15 | 10 | 0 | 10 | 0 |
| | TNTC | 10 | 10 | 15 | 10 | 10 | 10 | 0 | 10 | 0 |
| | 120–185 | 10 | 5 | 10 | 1 | 10 | 10 | 0 | 10 | 0 |
| | | | 4 | 7 | 5 | 7 | | | | |
| | | | 1 | 5 | 2 | 4 | | | | |
| CDC No. 111 | TNTC | 10 | 10 | 20 | 10 | 20 | 2 | 15 | 10 | 0 |
| | | | | | | | 2 | 10 | | |
| | | | | | | | 6 | 5 | | |
| | TNTC | 10 | 8 | 15 | 10 | 15 | 5 | 10 | 10 | 0 |
| | | | 2 | 4 | | | 1 | 5 | | |
| | | | | | | | 2 | 4 | | |
| | | | | | | | 2 | 0 | | |
| | 86–164 | 10 | 9 | 15 | 9 | 15 | 2 | 3 | 10 | 0 |
| | | | 1 | 10 | 1 | 10 | 8 | 0 | | |

12. Culturing means as claimed in claim 7 wherein said polyhydric alcohol is present in said aqueous liquid at a concentration of between about 1 and about 6 percent by weight to volume.

13. Culturing means as claimed in claim 7 wherein said water-absorbent matrix is formed of bibulous paper.

14. Culturing means as claimed in claim 7 for culturing said microorganism in an environment enriched with a gas, said means additionally comprising a gas generating composition and enclosure means for said matrix and said gas generating composition.

15. Culturing means as claimed in claim 14 additionally comprising a base member for carrying said matrix.

16. Culturing means as claimed in claim 15 wherein said base member is provided with a vented cover member, forming therewith a test device, said means additionally comprising a gas generating composition and enclosing means for said test device and gas generating composition.

17. Culturing means as claimed in claim 16 wherein said gas generating composition is in the form of a tablet and wherein said enclosing means is a sealable envelope.

18. Culturing means as claimed in claim 17 wherein said microbiological nutrient material incorporated with said matrix is selective for *Neisseria gonorrhoeae* and wherein the gas is released by said gas generating composition is carbon dioxide.

19. A test kit for the presumptive identification of *Neisseria gonorrhoeae* comprising the culturing means of claim 18 and a cytochrome oxidase indicator.

20. Culturing means as claimed in claim 15 wherein said gas generating composition is also carried by said base member and wherein said enclosing means comprises a cover member cooperable with said base member to form therewith a chamber enclosing said matrix and said gas generating composition.

21. Culturing means as claimed in claim 20 wherein said microbiological nutrient material incorporated with said matrix is selective for *Neisseria gonorrhoeae* and wherein the gas released by said gas generating composition is carbon dioxide.

22. A test kit for the presumptive identification of *Neisseria gonorrhoeae* comprising the culturing means of claim 21 and a cytochrome oxidase indicator.

* * * * *